(12) United States Patent
Nonomura

(10) Patent No.: US 10,786,524 B2
(45) Date of Patent: *Sep. 29, 2020

(54) CYTOCHROME P450 ENZYME COMPLEXES AND METHODS OF TREATMENT USING THE SAME

(71) Applicant: Innovation Hammer LLC, Powell, OH (US)

(72) Inventor: Arthur M. Nonomura, Litchfield Park, AZ (US)

(73) Assignee: Innovation Hammer LLC, Powell, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/666,692

(22) Filed: Oct. 29, 2019

(65) Prior Publication Data

US 2020/0061096 A1    Feb. 27, 2020

Related U.S. Application Data

(60) Continuation of application No. 15/677,381, filed on Aug. 15, 2017, now Pat. No. 10,493,090, which is a continuation of application No. 13/748,990, filed on Jan. 24, 2013, now abandoned, which is a division of application No. 12/653,052, filed on Dec. 8, 2009, now abandoned, which is a division of application
(Continued)

(51) Int. Cl.
| | |
|---|---|
| *A61K 31/7072* | (2006.01) |
| *A23L 33/12* | (2016.01) |
| *A23L 33/13* | (2016.01) |
| *A61K 35/60* | (2006.01) |
| *C12N 9/02* | (2006.01) |

(52) U.S. Cl.
CPC .......... *A61K 31/7072* (2013.01); *A23L 33/12* (2016.08); *A23L 33/13* (2016.08); *A61K 35/60* (2013.01); *C12N 9/0077* (2013.01); *A23V 2002/00* (2013.01)

(58) Field of Classification Search
None
See application file for complete search history.

(56) References Cited

U.S. PATENT DOCUMENTS

| | | |
|---|---|---|
| 5,445,826 A | 8/1995 | Kuhrts |
| 5,597,595 A | 1/1997 | Dewille et al. |
| 5,958,104 A | 9/1999 | Nonomura et al. |

(Continued)

FOREIGN PATENT DOCUMENTS

CN    1288693 A    3/2001

OTHER PUBLICATIONS

European Communication dated Sep. 25, 2009 in corresponding European patent application No. EP 05857145.6.
(Continued)

*Primary Examiner* — Tamra L. Dicus
(74) *Attorney, Agent, or Firm* — Nields, Lemack & Frame, LLC

(57) ABSTRACT

The present invention provides methods and compositions for balancing electron reduction potentials of formulations in a manner that reduces susceptibility to changes from xenobiotics. The present invention also provides novel compositions of matter based on structuring from a mobile nucleotide integral to its architecture.

11 Claims, 1 Drawing Sheet

Related U.S. Application Data

No. 11/312,056, filed on Dec. 20, 2005, now abandoned.

(60) Provisional application No. 60/638,918, filed on Dec. 23, 2004.

(56) References Cited

U.S. PATENT DOCUMENTS

| | | | |
|---|---|---|---|
| 6,020,288 | A | 2/2000 | Nonomura et al. |
| 6,037,375 | A | 3/2000 | Sakamoto et al. |
| 6,318,023 | B1 | 11/2001 | Yamashita |
| 6,514,544 | B2 | 2/2003 | Fuchs et al. |
| 6,660,293 | B2 | 12/2003 | Giordano et al. |
| 10,493,090 | B2 | 12/2019 | Nonomura |
| 2002/0064566 | A1 | 5/2002 | Beckett |
| 2004/0059110 | A1 | 3/2004 | Nakano et al. |
| 2004/0086574 | A1 | 5/2004 | Giordano et al. |
| 2006/0140927 | A1* | 6/2006 | Nonomura ............. A23L 33/12 424/94.4 |
| 2007/0248693 | A1 | 10/2007 | Mazzio et al. |
| 2010/0129890 | A1 | 5/2010 | Nonomura et al. |
| 2013/0137655 | A1 | 5/2013 | Nonomura et al. |
| 2017/0368092 | A1 | 12/2017 | Nonomura |

OTHER PUBLICATIONS

European Communication dated Dec. 22, 2009 in corresponding European patent application No. EP 05857145.6.
European Communication dated May 11, 2011 in corresponding European patent application No. EP 05857145.6.
International Search Report and Written Opinion dated Jul. 1, 2008 in corresponding PCT application No. PCT/US05/46124.
International Preliminary Report on Patentability completed Sep. 24, 2008 in corresponding PCT application No. PCT/US05/46124.
The Journal of Biological Chemistry, vol. 273, No. 27, Issue of Jul. 3, 1998, pp. 17036-17049, "Identification of the Binding Site on Cytochrome P450 2B4 for Cytochrome b5 and Cytochrome P450 Reductase", Bridges, et al.
Biochimica et Biophysica Acta, 1993, V. 1161, pp. 73-78, "The one-electron reduction potential of several substrates can be related to their reduction rates by cytochrome P-450 reductase", Butler, et al.
Annual Review of Pharmacology and Toxicology, vol. 45, 2005, pp. 1-25, "Cytochrome P450: Nature's Most Versatile Biological Catalyst", XP-002545171, Coon.
The Journal of Biological Chemistry, vol. 277, No. 32, Issue of Aug. 9, 2002, pp. 28351-28363, "Enzyme Ingenuity in Biological Oxidations: a Trail Leading to Cytochrome P450", Coon.
Archives of Biochemistry and Biophysics, V. 152, Issue 1, Sep. 1972, pp. 199-215, 2-pg. Abstract, "A comparison of microbody membranes with microsomes and mitochondria from plant and animal tissue", Donaldson, et al.
Archives of Biochemistry and Biophysics, vol. 333, No. 1, Article No. 0395, Sep. 1, 1996, pp. 308-315, "The Interaction of NADPH-P450 Reductase with P450: An Electrochemical Study of the Role of the Flavin Mononucleotide-Binding Domain", XP-002544866, Estabrook, et al.
http://www.healthline.com/health/what-is-liver-extract?, What Is Liver Extract? by Summer Fanous, pp. 1-3, Nov. 25, 2014.
Eur. J. Biochem, vol. 270, 2003, pp. 1164-1175, "Detemination of the redox potentials and electron transfer properties of the FAD- and FMN-binding domains of the human oxidoreductase NR1", Finn, et al.
The Journal of Biological Chemistry, vol. 277, No. 31, Issue of Aug. 2, 2002, pp. 27725-27732, "Cytochrome P450 cin (CYP176A), Isolation, Expression, and Characterization", Hawkes, et al.
Annals of Botany, vol. 83, 1999, pp. 551-557, "Possible Roles of Methyl Glucoside and Myo-inositol in the Opening of Cut Rose Flowers", Ichimura, et al.

Drug Metabolism and Disposition, vol. 28, No. 1, 2000, pp. 73-78, "Identification of Cytochrome P-450 Isoform(s) Responsible for the Metabolism of Pimobendan in Human Liver Microsomes", Kuriya, et al.
Proceedings of the National Academy of Sciences, vol. 101, No. 9, Mar. 2, 2004, pp. 2939-2944, "Structural and functional divergence of insect CYP6B proteins: From specialist to generalist cytochrome P450", Li, et al.
Methods in Enzymology, vol. 72, 1981, General Analytical Methods, pp. 296-303, "[16] Protein Determination in Membrane and Lipoprotein Samples: Manual and Automated Procedures", Markwell, et al.
Biochemical Society Transactions, vol. 33, Part 4, 2005, pp. 796-801, "Biodiversity of cytochrome P450 redox systems", McLean, et al.
Methods in Plant BioChemistry, vol. 9, 1993, pp. 261-279, "[10] Cytochrome P-450 Terpene Hydroxylases", Mihaliak, et al.
Journal of Neurochemistry, vol. 78, 2001, pp. 121-128, "Induction of NADPH cytochrome P450 reductase by the Alzheimer B-protein. Amyloid as A 'foreign body", Papolla, et al.
Plant Physiology, vol. 109, 1995, pp. 1483-1490, "Differential Induction of Cytochrome P450-Mediated Triasulfuron Metabolism by Naphthalic Anhydride and Triasulfuron", Persans, et al.
Methods in Enzymology, vol. 206, 1991, pp. 577-587, "[56] Isolation of P450 Enzymes from Human Liver", Raucy, et al.
Plant Physiology, vol. 130, Dec. 2002, pp. 1837-1851, "Cloning, Functional Expression and Subcellular Localization of Multiple NADPH-Cytochrome P450 Reductases from Hybrid Poplar", Ro, et al.
Proceedings of the National Academy of Sciences USA, vol. 96, Mar. 1999, pp. 1863-1868, "Structure of a cytochrome P450-redox partner electron-transfer complex", Sevrioukova, et al.
Insect Biochem. Molec. Biol., vol. 28, No. 1, 1998, pp. 1-9, Cytochrome P450 Purification and Immunological Detection in an Insecticide Resistant Strain of German Cockroach (*Blattella germanica*, L.), Scharf, et al.
Proceedings of the National Academy of Sciences USA, vol. 90, Apr. 1993, pp. 2890-2894, Plant Biology, "Purification, characterization, and cDNA cloning of an NADPH-cytochrome P450 reductase from mung bean", Shet, et al.
Cytochrome P450: Structure, Mechanism, and BioChemistry, Second Edition, 1995, Edited by Paul R. Ortiz de Montellano, Chapter 7, pp. 225-244, "NADPH Cytochrome P450 Reductase and Its Structural and Functional Domains", Strobel, et al.
Cytochrome P450: Structure, Mechanism, and BioChemistry, Second Edition, 1995, Edited by Paul R. Ortiz de Montellano, Chapter 6, pp. 183-223, "Structures of Eukaryotic Cytochrome P450 Enzymes", Von Wachenfeldt, et al.
Proceedings of the National Academy of Sciences USA, vol. 94, Aug. 1997, pp. 8411-8416, XP003007533, "Three-dimensional structure of NADPH-cytochrome P450 reductase: Prototype for FMN- and FAD-containing enzymes", Wang, et al.
J. Phys. Chem. Ref. Data, vol. 18, 1989, pp. 1637-1755, "Reduction Potentials of One-electron Couples Involving Free Radicals in Aqueous Solution", Wardman, et al.
Genome Biology, vol. 1, No. 6, 2000, pp. 1-9, "Cytochrome P450: A Success Story", Werck-Reichhart, et al.
The Journal of Biological Chemistry, vol. 251, No. 17, Issue of Sep. 10, 1976, pp. 5337-5344, "Some Properties of a Detergent-solubized NADPH-Cytochrome c (Cytochrome P-450) Reductase Purified by Biospecific Affinity Chromatography", Yasukochi, et al.
Splenda, https://www.splenda.com/faq/no-calorie-sweetener/#what-is-splenda-brand-sweetener-sucralose, pp. 1-3, 1996-2015.
Office Action dated Feb. 12, 2008 in related U.S. Appl. No. 11/312,056.
Office Action dated Jun. 26, 2008 in related U.S. Appl. No. 11/312,056.
Final Rejection dated Jul. 9, 2009 in related U.S. Appl. No. 11/312,056.
Office Action dated Sep. 28, 2011 in related U.S. Appl. No. 12/653,052.
Office Action dated Mar. 28, 2012 in related U.S. Appl. No. 12/653,052.

(56) References Cited

OTHER PUBLICATIONS

Final Rejection dated Oct. 25, 2012 in related U.S. Appl. No. 12/653,052.
Office action dated Apr. 22, 2014 in related U.S. Appl. No. 13/748,990.
Final rejection dated Nov. 6, 2014 in related U.S. Appl. No. 13/748,990.
Office action dated Mar. 4, 2015 in related U.S. Appl. No. 13/748,990.
Final rejection dated Sep. 28, 2015 in related U.S. Appl. No. 13/748,990.
Office action dated Jan. 29, 2016 in related U.S. Appl. No. 13/748,990.
Final rejection dated Jul. 26, 2016 in related U.S. Appl. No. 13/748,990.
Office action dated Dec. 15, 2016 in related U.S. Appl. No. 13/748,990.
Final rejection dated May 17, 2017 in related U.S. Appl. No. 13/748,990.

* cited by examiner

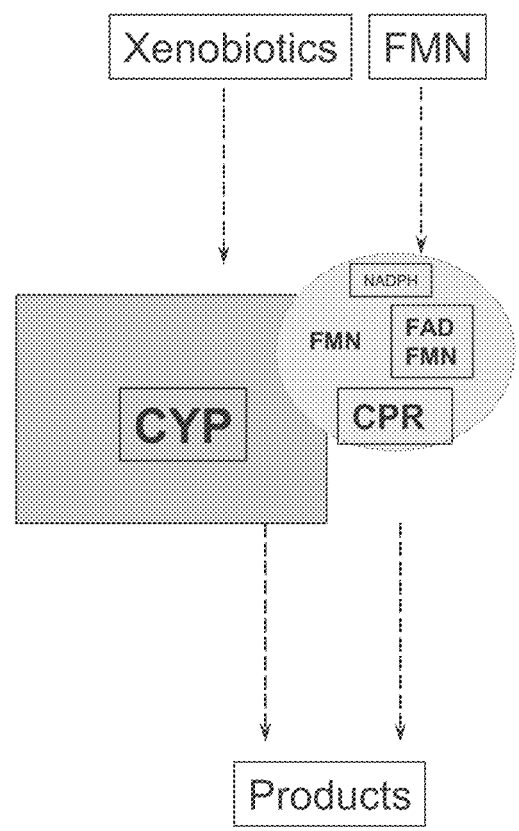

CYTOCHROME P450 ENZYME COMPLEXES AND METHODS OF TREATMENT USING THE SAME

This application is a continuation of U.S. patent application Ser. No. 15/677,381 filed Aug. 15, 2017, which is a continuation of U.S. patent application Ser. No. 13/748,990 filed Jan. 24, 2013, which is a divisional of U.S. patent application Ser. No. 12/653,052 filed Dec. 8, 2009, which is a divisional of U.S. patent application Ser. No. 11/312,056 filed Dec. 20, 2005, which claims priority of provisional application Ser. No. 60/638,918, filed Dec. 23, 2004, the disclosures of which are hereby incorporated by reference.

BACKGROUND OF THE INVENTION

The present invention relates generally to methods and compositions for treating living organisms.

Upon utilization of a nanoscalar particle to achieve a practical purpose, its design and replication defines the field of nanotechnology. Indeed, over the past decade, inventions of biomaterials have focused on synthesis, while purposeful in vivo applications have gone wanting. Developments have resulted from the fabrication of novel architectures that range from Bucky Balls to octahedral DNA. Cytochromes offer some special nanometric advantages that are realized as a result of architecture elucidated within the current invention A diversity of cytochromes present possibilities for multitudes of combinations. For example, linkage of chemical reduction of dioxygen to electrogenic translocation of protons across a membrane occurs through Cytochrome C (Cc) oxidase (A. Namslauer, A. S. Pawate, R. B. Gennis and P. Brzezinski (2003) Redox-coupled proton translocation in biological systems: Proton shuttling in cytochrome c oxidase PNAS 100(26):15543-15547) and if Cc, for instance, is singled out from all other cytochromes for consideration, over three score evolutionary lines are documented, a diversity that offers many avenues of process.

Cytochromes P450 (P450) are hemoproteins that catalyze monooxygenation of endogenous and xenobiotic hydrophobic substrates. Families of P450 have a broad range of substrates and are responsible for processing metabolic quantities of exogenous compounds by inserting singlet oxygen that renders them soluble for removal. The utilization of oxygen by P450 mediates hydroxylations, epoxidations, dehalogenations, deaminations and dealkylations. The predominance of literature is devoted to P450 monoxygenases (CYP); however, electron reduction must, necessarily, be balanced by coupling reactions with NADPH:Cytochrome P450 reductases (CPR). P450 is understood as an enzyme complex of CYP and CPR.

The present invention generally relates to cytochromes, particularly cytochromes P450. Specifically, the invention is of primary application for electron reduction potential mechanisms that activate the induction, building, and accurate architectural reproduction by over fifty functionally different structures of P450 Each monooxygenase is substrate specific and, coupled with CPR, may be read spectrophotometrically at 450 nm in the presence of carbon monoxide and, for example, nitrobenzoate.

In particular, the present inventor has determined that small quantities of xenobiotics, such as carcinogens and drugs, can be recognized, deactivated and prepared for removal by P450 systems. Although, some substrates are beneficial, others are toxins, mutagens, or carcinogens.

It is in the best interest of humanity to maintain P450 systems at optimal levels to metabolize and remove physiological concentrations of objectionable substances. The majority of xenobiotics, being unavoidable through environmental, gustatory, and pharmaceutical exposures, may be processed at some point of metabolism by P450. On the other hand, inhibitors of P450 are also unavoidable. Upon exposure to the strongest inhibitors, the population is left without the ability to defend adequately against xenobiotics. Until the discoveries of the present invention, a means of re-establishing and/or fortifying P450 to process xenobiotics in living animals had not been made available.

SUMMARY OF THE INVENTION

This invention elucidates a design philosophy that when applied to cytochromes, deals with physiologically important xenobiotics effectively. In certain embodiments, building and increasing quantities of most of the known P450 structures is accomplished in vivo as a consequence of cascading responses to architectural modification, primarily, with the nucleotide, flavin mononucleotide (FMN), within CPR. As these nucleotides are administered into living systems, they move across the surface of reductases as they become integral to the structure and function of entire monooxygenase-reductase complexes, primarily as P450 plus the added FMN (P450:FMN) (or other suitable oxidant).

Thus, a P450:FMN enzyme complex, with more than one FMN molecule in the complex, results in a novel composition of matter (such as in the form of a food supplement, a dietary supplement, a beverage, a topical formulation, or a pill) that assists the body in detoxifying xenobiotics. The direct connection of FMN, for example, to fortify these enzyme complexes, has not been made previously. This invention thus provides methods of detoxification by administering compositions that are selected for accelerating specific activity. These formulations enhance P450 in subcellular nanoarrays. By means of compositions comprised of inducers that are selected for regeneration, the present invention introduces methods of activating repressed nanoscopic structures.

For these reasons, it would be desirable to provide novel methods and compositions for the purpose of fortifying the complexes in humans and other living organisms. It would be particularly desirable if such methods and compositions were able to induce these complexes in specific tissues. The present invention further provides convenient methods resulting in fortification of these complexes for animal and human therapy. It is desirable that the methods and compositions of the present invention promote eradication of undesirable compounds in a manner that enhances the quality of life. It would be further desirable to provide palatable treatments that are nutritious and broadly effective. To that end, preferably, the compositions of an embodiment of the present invention are sweet-tasting, as a rewarding means that encourage daily upkeep of the enzymes complexes.

As a first aspect, the present invention provides isolated P450:FMN compositions of matter wherein there is a plurality of FMN molecules in the enzymatic complex. The methods of isolation, such as from urine or the liver of an animal, are well known to those skilled in the art.

As a second aspect, the present invention provides a method for enhancing P450 family members, numbering over 50, by treatment with their corresponding oxidants. The method comprises administering to an animal in need thereof oxidants that increase the quantity of the complex in that animal.

As a third aspect, the present invention provides compositions for inducing P450:FMN enzyme complexes.

As a fourth aspect, the present invention provides compositions for enhancing anticarcinogenic enzyme complexes in humans. The compositions comprise an effective amount of a nucleotide that increases the amount of the complexes in vivo.

As a fifth aspect, the present invention provides compositions comprising a first compound selected from the group consisting of CPR and oxidants that induce P450:FMN enzyme complexes.

As a sixth aspect, the present invention provides methods for the automatic fortification of P450:FMN enzyme complexes in living systems. The methods include treatment with a compound selected from the group consisting of one or more structural components of the enzyme complexes.

As a seventh aspect, the present invention provides a method for improving the chemical defense of humans and animals using P450:FMN enzyme complexes. The method includes the step of administering to a human or animal in need thereof an effective amount of a composition comprising FMN.

As another specific aspect, the present invention provides methods for dietary supplements to come to the defense of humans against harmful xenobiotics whilst improving nutrition, particularly, in sweeteners.

Compositions are provided that comprise naturally sweet reductants with natural oxidants for increasing the amount of P450:FMN enzyme complexes in an animal.

These and other aspects of the present invention are described further in the detailed description and examples of the invention which follow.

BRIEF DESCRIPTION OF THE DRAWING

FIG. 1 is a simplified and integrated schematic depiction of the enzyme complex of the invention. At the top center of the FIGURE is supplemental FMN, that is processed and integrated into native P450 yielding P450:FMN of the present invention. Products are given at the bottom center of the FIGURE. Fortification of the complex is achieved by administration of effective therapeutic dosages of one or more components of the complex.

DETAILED DESCRIPTION OF THE INVENTION

According to the present invention, nanoscalar methods, compositions, and systems are provided that induce P450. Methods are provided for treatment, particularly for those who are compromised by exposure that requires therapy by administration of the compositions of the present invention.

The subject invention provides tools and methodologies for activating production of structures from nucleotides, enzymes and their substrates. Of particular note, a number of nucleotides, most often as several FMNs, occur as mobile components of the enzyme complex. The subject invention represents a significant contribution to fields of nutrition, nutraceuticals, dietary supplements, pharmaceuticals, cosmetics, prophylaxis, and medicine. Acceleration by formulation of nutritive oxidants with reductants contributes to distribution.

Accordingly, the present invention provides methods for treating animals, for increasing the amount of cytochrome P450 in animals, and for enhancing the ability of an animal to detoxify xenobiotics. The present invention also provides compositions and formulations for administration to animals in need thereof, or as a prophylaxis, in order to increase the amount of cytochrome P450 in the body of the animal. An exemplary nutritive formulation includes a selection of a slow-release niacin with a palatable reductant, preferably a self-rewarding sweetener, such as glucose.

Unless otherwise defined, all technical and scientific terms employed herein have their conventional meaning in the art. As used herein, the following terms have the meanings ascribed to them.

Enzymatic complexes as used herein refers to the complete and functional P450:FMN quaternary structure, wherein, the preferred molecular complex is modified with a plurality of FMN molecules. In accordance with the present invention, these complexes are fortified, or strengthened, in a manner that promotes, increases and improves rates of reaction of P450s.

"Oxidant" refers to an electron acceptor of CPR.

"Reductant" refers to electron donors or oxidase substrates that induce CYP. Oxidase substrates, which induce CYP accelerate the metabolism of oxidants by CPR.

"Inducer" refers to oxidants and reductants that improve the metabolic capacity of P450s. Induction involves a given substrate, enhancing the specific activity of the P450s.

"P450:FMN" refers to a P450 enzyme complex with more than one FMN. "Cc" refers to Cytochrome C.

"Animal" refers to virtually all living biota of the kingdom of animals capable of receiving treatments, particularly humans, their pets, and livestock.

"Live organism" refers to all living organisms.

"Percent" or "%" is percent weight.

"ppm" refers to parts per million.

"g" refers to grams.

"mg" refers to milligrams.

"mcg" refers to micrograms.

"Sweetener" includes, but is not limited to, the following: natural sugars, for example, pentose, hexose, disaccharide, and oligosaccharide; and artificial sweeteners, for example, sucralose, saccharin, and aspartame. Natural sugars may further include: xylose, arabinose, fructose, glucose, mannose, galactose, sucrose, maltose, xylitol, and the like. The terms sweeteners may also include mixtures of one or more natural sugars and/or one or more artificial sweeteners.

The compositions and methods of the present invention may be administered by any therapeutically effective route of administration, including but not limited to oral, sublingual, rectal, parental (subcutaneous, intramuscular, intravenous), transdermal, topical, nasal, aerosol and like forms of administration. Dosage forms include tablets, troches, suspensions, solutions, capsules, powders, microencapsulated systems, various transdermal delivery systems, and the like. Topical and oral administrations are particularly preferred.

In particular, they may be advantageously administered to humans, animals, and protistans, alike because of the universality of cytochromes P450. The methods and compositions of the preferred embodiment of the present invention may be used to enhance defense mechanisms of xenobiotics in humans and their domesticated animals. Where metabolism of medicines may be affected by prior exposure to P450 inhibitors, the methods and compositions of the present invention may be used, furthermore, to assist with determination of baselines for dosage of pharmaceuticals that may be metabolized by P450.

As provided herein, fortification focuses on modulating electron transfer through the enzymatic complexes in a manner that shifts the flow of electrons. FIG. 1 is a schematic depiction of the electron transfer to the catalytic cycle of a single complex. By accelerating or adding to the CPR of an organ or tissue, reductive capacity is enhanced. An enhanced pool allows increased capacity for electron transfer. Accordingly, the compositions and methods of the present invention may include inducers or oxidants as integral structural components.

Methods and Compositions

The present invention provides methods for administering substrates that are designed to modify the architecture of P450s and fortify P45:FMN complexes in animals, including humans. These methods typically involve administration of an oxidant component and may, preferably, include administration of an oxidant that is a component of the complex. Oxidants may be formulated with appropriate reductants for balanced therapy and co-induction of monooxygenases and reductases.

Oxidants

Suitable oxidants are compounds that induce NADPH: cytochrome P450 reductase. Any compound capable of inducing such reductases will be useful as the oxidant component in the methods, compositions, and systems of the present invention. Accordingly, reductases, particularly those capable of receiving FMN and nicotinic acids, may be utilized as the oxidant component of the methods, compositions, and systems of the present invention. In addition, a number of other suitable oxidants will be readily determinable by those skilled in the art.

Preferred oxidant compounds exhibit a one-electron reduction potential ($E_0$) between about −400 mV and about −165 mV inclusive, more preferably between about −396 mV and about −240 mV. Multiple electron reductions are biologically important with P450 and oxygen. Examples of suitable oxidants include, but are not limited to, ferredoxin-NADP+ reductases and NADPH:cytochrome P450 reductase including the reductases listed hereinabove, as well as flavins, nucleotides, nitrobenzoates, nicotinic acids, nitrobenzoic acids, ammonium salts, menadione, amine oxides, formamidines, cytochrome reductases, and slow-release formularies, salts, hydrates, aldehydes, esters, amines, amides, alcohols, derivatives, dietary supplements and other biologically or chemically equivalent derivatives thereof and combinations thereof.

Specific examples of flavins which are useful as oxidants in the methods and compositions of the present invention include, but are not limited to, riboflavin, flavin mononucleotide (FMN), menadione, deazaflavin, lumichrome, lumizine, flavin adenine dinucleotide (FAD), alloxazine, salts, hydrates, derivatives and combinations thereof. Specific examples of ammonium compounds include, but are not limited to ammonium sulfate, ammonium chloride, ammonium hydroxide, urea, amines, and the like. Specific examples of cytochrome reductases include, but are not limited to, cytochrome f, Cc, cytochrome b5, flavocytochrome P450, nitric oxide synthase, and combinations thereof. Specific examples of nicotinic acids include but are not limited to NicoSpan, NiaSpan, niacin, NAD, NADH, NADP, NADPH and combinations thereof. Examples of preferred oxidants, whose selection is based on $E_0$ (values) and beneficial metabolism, include nitrobenzoate (−396 mV), FMN (−313 mV), glycolate (α) (−290 mV), riboflavin (−292 mV), and salts, hydrates and derivatives of any of the above.

Currently preferred oxidants for use in the methods and compositions of the present invention include but are not limited to FMN, NiaSpan, NAD/NADH, menadione, ammonium sulfate, α, and salts, hydrates and derivatives thereof FMN and nicotinic acids are particularly preferred oxidants in the compositions, methods and systems of the present invention, primarily because they are cost effective and generally regarded as safe. Additionally, organ products such as whole liver, dry liver pills, liver oils and liver extracts are excellent sources of undefined cytochromes, oxidants, and reductants. Where organ products are unpalatable or are problematic because of, for instance, cholesterol or gout, it would be advisable to avoid these types of products. Moreover, in the course of processing, proteins and nucleotides may be denatured; thus, organ-derived products may require supplementation with oxidants. FMN is the particularly preferred oxidant.

As noted above, oxidants are employed solely or, they may comprise any one or more of the foregoing oxidants in combination with a reductant or other oxidants. For example, in one preferred embodiment, the oxidant comprises a combination of FMN and fish oil concentrate. In the embodiment of the invention wherein two or more oxidants are combined, they are typically equimolar provisions of the oxidant component of the compositions and methods of the present invention.

Inhibitors

A partial list of inhibitors includes the following common items: foods and beverages, including grapefruit, turmeric (curcuminoids), bergamottin (flavoring in Earl Grey Tea), and well-water (arsenic); drugs, such as, antibiotics (ciprofloxacin, erythromycin, chloramphenicol, and the like), antivirals (ritonavir, etc.); contraceptives (ethynylprogesterone, and the like), antimycotics (ketoconazole, itraconazole, terconazole, miconazole, and the like), chemotherapies (aminoglutethimide, etc.); acid reflux (cimetidine), bioassays (metyrapone, diethyldithiocarbamate), barbiturates and mood drugs (secobarbital, Prozac, Zoloft, Luvox and the like); cosmetics (hydrogen peroxide, dental whitener, bleach, etc.); air pollution from carbon monoxide and other components of smog; insecticides (cyanides, parathion, piperonyl butoxide, etc.); and acyl hydrazine, alkyl hydrazine, aryl hydrazine, allylisopropylacetamide, carbon disulfide, carbon tetrachloride, dichloroacetamides, dihydropyridine, di sulfiram, isothiocyanate, mercaptosteroid, phenylimidazole, phenelzine, phenylphenanthridinone, quinolones, syndones, thiourea, tienilic acid, and undecynoic acid.

In a physiological sense, constant exposure to inhibitors renders the general population susceptible to xenobiotics. When P450 is inhibited, it is imperative to resurrect dysfunctional P45:FMN complexes by the compositions and methods of the present invention, if for no other reason than to reduce susceptibility to carcinogens. Inhibitors include compounds that degrade or bind to the heme iron atom or to the prosthetic heme group. Others may be competitive inhibitors of P450, the effects of which may last the half life of a drug.

Application

The oxidants are, by themselves useful in methods of treatment and in methods of fortifying the P40 enzyme complexes. For example, flavins, by themselves, or together with suitable excipients and/or carriers, are useful in the methods of the present invention. Although the oxidant components may be applied in a solid form, it is sometimes advantageous to provide oxidants in liquid form, such as by solubilizing the component in an aqueous or suitable organic solvent or carrier to produce aqueous or organic solutions of the oxidants. The amount of oxidant that is solubilized in the carrier will depend upon the particular oxidant selected and the method of application. The oxidant may be solubilized in the carrier by adding the oxidant to the carrier and allowing the oxidant to dissolve. In some instances, the application of stirring, agitation, or even heat may facilitate the dissolution of the oxidant in the carrier.

For example, suitable formulations are not particularly limited, and include solutions of the oxidant dissolved in a suitable carrier. For example, FMN can be dissolved in a carbonated beverage with or without a reducing sugar such as xylose and/or glucose. The carbon dioxide inhibits premature oxidation of the FMN. FMN in combination with chocolate is another example, such as a formulation comprising 0.2 to 0.5 mg FMN per 30-60 grams of chocolate, preferably dark chocolate. Yet other suitable formulations include the oxidant and one or more reducing sugars, artificial or natural, as discussed above. Still further suitable formulations include emulsions, such as FMN and fish oil, cod liver oil or both. These emulsions can be formulated in a capsule and administered orally. Another suitable formulation is FMN and red wine.

The oxidant can be administered in a carrier to create a formulation having an oxidant concentration in the range between about 0.0001% and about 100% by weight of the composition inclusive, preferably between about 0.01% and about 100% inclusive. For example, because ethanol is an inducer of CYP2E1, a flavin:alcohol beverage ratio of 1:1000 is preferred to match ratios generally found to induce the enzyme complex. An exemplary skin cream comprising 0.1% to 1% α-hydroxy is suitable for topical application when formulated with 0.001% to 0.005% riboflavin.

Compositions of the present invention may also include any of a variety of excipients, which improve or at least do not hinder the beneficial effects of the compositions of the present invention. While the compositions of the present invention may consist essentially of oxidants, compounds may be formulated in suitable excipients. In the embodiment wherein the oxidant is a single composition for use in the methods of the present invention, the composition may include excipients having solubilized, dispersed, supported, or otherwise contained therein, an amount of the oxidant that induces cytochrome P450. A solution containing oxidants may be prepared using the general techniques set forth above.

Compositions containing oxidants in a single solution may include any combination of oxidants selected from those described hereinabove. Preferred oxidants for one-step compositions include, but are not limited to FMN and nicotinic acids. For example, one composition according to the present invention includes menadione and niacin. Another composition according to the present invention includes FMN and cod liver oil. Another composition according to the present invention includes daily 50 mg riboflavin and 5 mg NADP. Another composition according to the present invention includes 1 mg FMN cloaked in carbon dioxide as a stabilizing excipient and to be taken up to 5 times daily.

Compositions of oxidants will typically be administered at a concentration ranging between about 1 mg and about 1000 mg per dose. Preferred combined oxidant compositions include: (1) 5 mg NADH and 25 mg niacin; (2) 5 mg FMN and 50 mg slow-release niacin; and (3) 3 mg FMN and 500 mg fish oil concentrate. Macromolecules such as CPR and CYP pose problems of stability and may require cold storage and inert environments. Formulation with carbonates or bicarbonates prevents oxidation. The compositions of the present invention may also be applied topically in appropriate dermatological or optical formulations.

Compositions according to the present invention may find specifically tailored utilization, including enhanced performance of NADPH:cytochrome P450 reductase; enhanced quantity of NADPH:cytochrome P450 reductase; fortification of P450:FMN enzyme complexes; inducing such complexes after exposure to inhibitors; reduced susceptibility to carcinogens; and for therapy. Compositions may also be formulated at very low concentrations of FMN or in sustained release dosages of niacin for daily enhancement.

The aqueous solutions employed in the systems of the present invention may be formulated in the same manner as described hereinabove for compositions, using the same types of aqueous carriers. Preferably a pharmaceutically acceptable carrier is used. One preferred formulation according to the present invention includes flavin mononucleotide as the oxidant. Another preferred formulation according to the present invention includes niacin as the oxidant. Another preferred system according to the present invention includes flavin mononucleotide and liver extracts as oxidants. Another formulation according to the present invention includes oxidants formulated with reductants such as, reducing sugars; the preferred formulation utilizing treatment with 1 mg to 100 mg NiaSpan, sustained release niacin, as an oxidant formulated with 10 g to 1000 g of a pentose reductant such as xylose.

The following examples are provided to further illustrate the present invention, and should not be construed as limiting thereof. The present invention is defined by the claims, which follow.

In these examples, reagents, biochemicals, and dietary supplements were obtained in purest form available, and were obtained as reagent grade and USP chemicals where possible. Purified P450s including recombinant human NADPH:Cytochrome P450 Reductase (hCPR) were obtained from PanVera.

In these examples, "L" means liter; "ml" means milliliter; "cm" means centimeter; "$cm^2$" means centimeters squared; "nm" means nanometer; "M" means molar; "mM" means millimolar; "μM" means micromolar; "nM" means nanomolar; "mol" means moles; "μmol" means micromoles; "mg/ml" means milligrams per milliliter; "$ml/cm^2$" means milliliters per centimeter squared; "kDa" means kiloDaltons; "L/min" means liters per minute; "d" means days; "h" means hours; "min" means minutes; "s" means seconds; "g" means multiple of centrifugal gravitational force; "°" means degrees centigrade; CYP is a cytochrome P450 monooxygenase; CPR is NADPH:cytochrome P450 reductase; CPR is microsomal-CPR.

The following exemplary compositions are intended to provide further guidance to those skilled in the art, and do not represent an exhaustive listing of compositions within the scope of the present invention.

Example 1

First Exemplary Composition: FMN

| Composition | Concentration per dose | |
|---|---|---|
| | Broad Range | Narrow Range |
| FMN | 0.01-50 mg | 3-5 mg |
| Cod liver oil | 1-2500 mg | 100-1000 mg |

Second Exemplary Composition: Drink

| Composition | Concentration per 100 ml dose | |
|---|---|---|
| | Broad Range | Narrow Range |
| Xylose | 0.1-1% | 1-1000 g |
| FMN | 1-1000 ppm | 1 mcg-5 mg |

Third Exemplary Composition

| Component | Concentration | |
|---|---|---|
| | Broad Range | Narrow Range |
| FMN | 0.01-20 mg | 1-5 mg |
| Analgesics | 1-2000 mg | 5-100 mg |

Fourth Exemplary Composition

| Composition | Concentration | |
|---|---|---|
| | Broad Range | Narrow Range |
| FMN | 1-5 mg | 2-5 mg |
| NADP | 10-100 mg | 10-50 mg |
| Bicarbonate | excipient | excipient |

Fifth Exemplary Composition

| Component | Dose | Range |
|---|---|---|
| FMN | 5 mg | 1-5 mg |
| Liver extract | 1 mg | 10 mcg-2 g |

Sixth Exemplary Composition: Drink

| Composition | Concentration | |
|---|---|---|
| | Broad Range | Narrow Range |
| FMN | 1 mcg-50 mg | 10 mcg-5 mg |
| D-Xylose | 1-1000 g | 5-50 g |
| EtOH | excipient | excipient |
| Carbon dioxide | excipient | excipient |
| Water | excipient | excipient |

Seventh Exemplary Composition: Natural Sweetener Suitable for people with diabetes

| Composition | Concentration | |
|---|---|---|
| | Broad Range | Narrow Range |
| Folate | 1-100 mcg | 1-3 mcg |
| FMN | 1-8000 mcg | 1-100 mcg |
| D-Xylose | 1-1000 g | 5-50 g |

Eighth Exemplary Composition: Blended Diet Sweetener

| Composition | Concentration | |
|---|---|---|
| | Broad Range | Narrow Range |
| FMN | 1-1000 mcg | 2-200 mcg |
| D-Xylose | 1-1000 g | 5-50 g |
| Sucralose | 1-1000 g | 5-50 g |

Example 2

The following example illustrates an application of human P450 compositions according to the present invention. Procedures followed previously described methods, e.g., U.S. Pat. No. 6,020,288; M. Markwell, et al., Methods of Enzymology 72:296-303 (1981); C. A. Mihaliak, et al., Methods in plant biochemistry 19:261-279 (1993); R. Donaldson, et al., Arch. Biochem. Biophys. 152:199-215 (1972); and M. Persans, et al., Plant Physiol. 109:1483-1490 (1995)). The results demonstrate the efficacy of the methods and compositions of the present invention for the enhancement of P450 enzyme complexes.

Methods. CPR substrates have been assayed on various tissues (e.g., U.S. Pat. No. 6,020,288); therefore, response to human CPR (hCPR) was examined under controlled conditions on live index organisms. The direct effects of substrates on hCPR were measured by preparation of microsomes for quantification against CPR and Cc. Controls included equal concentrations of each individual treatment or substrate in surfactant and water. Untreated controls were maintained under identical conditions of culture. Oxidase activity of Cc was inhibited by potassium cyanide. The reaction was initiated by addition of Cc wherein NADPH-dependent reduction of Cc was monitored for increases in absorbance.

Results and Discussion. FMN showed over 4.5 times the induction of components tested. Cytochromes P450 enzyme complexes have defined catalytic electron transfer functions. See, C. von Wachenfeldt, et al., Structures of Eukaryotic Cytochrome P450 Enzymes, P. R. Ortiz de Montellano, ed. (1995) Cytochrome P450: Structure, Mechanism, and Biochemistry (Second Ed.), Plenum Press, New York, pp 183-223 and H. Strobel, et al., NADPH Cytochrome P450 Reductase and Its Structural and Functional Domains, P. R. Ortiz de Montellano, ed. (1995) Cytochrome P450: Structure, Mechanism, and Biochemistry (Second Ed.) Plenum Press, New York, pp 225-244. Combinations of cytochromes P450 are numerous and underscore the potential of the field. Selection of oxidants based on one electron reduction of compounds (see, e.g., Wardman, P. 1989, J Phys. Chem. Ref Data 18(4):1637-1755) within potentials associated with CPR reductase (see, e.g., Butler, J. et al. 1993 Biochimica et Biophysica Acta 1161:73) proved successful, test results showing that specific activity may be enhanced by FMN. Oxidants accelerate cytochrome P450 and, FMN, in particular, may fortify its integral structure. In some instances, enhancement of cytochromes other than CPR may be key. For example, Cc may accelerate response where CPR does not, and for those exceptional cases, broad spectrum dosage or specific agents will be the subject of further investigations. Even though the most potent treatment may be nanomolar cytochromes, of the integral components of cytochromes, FMN showed activity at sufficiently low concentrations to be a prime selection for practical, safe and effective therapies. P450 provides widespread applicability of compositions and methods for selection of components which may be utilized to endow animals with a means of resistance to xenobiotic stresses while gaining ever greater health.

What is claimed is:

1. A method of inducing P450:FMN complexes in an animal, comprising formulating a solid composition comprising bicarbonate as a stabilizing excipient, 1 mcg to 50 mg of FMN or a salt thereof protected by said stabilizing excipient, alloxazine, and a member selected from the group consisting of deazaflavin, ammonium sulfate, niacins and menadione; and administering to said animal said solid composition in an amount effective to induce P450:FMN complexes in said animal.

2. The method of claim 1, wherein said animal is a human.

3. The method of claim 1, wherein said solid composition further comprises a reducing sugar.

4. The method of claim 3, wherein said reducing sugar is xylose or glucose or combinations thereof.

5. The method of claim 2. wherein said solid composition further comprises a reducing sugar.

6. The method of claim 5, wherein said reducing sugar is xylose or glucose or combinations thereof.

7. The method of claim 1, wherein said solid composition is in the form of a member selected from the group consisting of tablets, troches, lozenges, capsules and powders.

8. The method of claim 1, wherein said solid composition is administered to said animal transdermally.

9. The method of claim 2, wherein said solid composition is administered to said human transdermally.

10. The method of claim 1, wherein said member is ammonium sulfate.

11. The method of claim 2, wherein said member is ammonium sulfate.

* * * * *